(12) United States Patent
Guirguis

(10) Patent No.: US 11,656,225 B2
(45) Date of Patent: May 23, 2023

(54) DUAL SWAB FLUID SAMPLE COLLECTION FOR SPLIT SAMPLE TESTING AND FINGERPRINT IDENTIFICATION DEVICE

(71) Applicant: Raouf A. Guirguis, Fond Du Lac, WI (US)

(72) Inventor: Raouf A. Guirguis, Fond Du Lac, WI (US)

( * ) Notice: Subject to any disclaimer, the term of this patent is extended or adjusted under 35 U.S.C. 154(b) by 0 days.

(21) Appl. No.: 16/737,238

(22) Filed: Jan. 8, 2020

(65) Prior Publication Data

US 2020/0141934 A1 May 7, 2020

Related U.S. Application Data

(62) Division of application No. 15/417,905, filed on Jan. 27, 2017, now Pat. No. 10,564,155.

(51) Int. Cl.
*G01N 33/543* (2006.01)
*B01L 3/00* (2006.01)
(Continued)

(52) U.S. Cl.
CPC ...... *G01N 33/54386* (2013.01); *B01L 3/5023* (2013.01); *B01L 3/5025* (2013.01);
(Continued)

(58) Field of Classification Search
CPC ............... G01N 33/54386; G01N 1/18; G01N 2001/028; B01L 3/5023; B01L 3/5025; B01L 3/5029; B01L 2300/0825; B01L 2400/0478; B01L 2200/141; B01L 2300/021; B01L 2300/042
See application file for complete search history.

(56) References Cited

U.S. PATENT DOCUMENTS 3,784,358 A 1/1974 Drake, Jr.
4,225,557 A 9/1980 Hartl et al.
(Continued)

FOREIGN PATENT DOCUMENTS

EP 0200381 11/1986
EP 0203238 12/1986
(Continued)

OTHER PUBLICATIONS

International Search Report; International Application No. PCT/US18/15508; International Filing Date; Jan. 26, 2018 2 pages.
(Continued)

*Primary Examiner* — Dennis White
(74) *Attorney, Agent, or Firm* — Cantor Colburn LLP

(57) ABSTRACT

An apparatus for testing a fluid sample including a sample receiving member having an opening for receiving a fluid sample, wherein the sample receiving member comprises at least a first and second sample collection chambers, a sample retention member, in fluid communication with the first sample collection chamber, to retain a portion of the fluid sample, and at least one test strip, in fluid communication with the second collection chamber, to indicate the presence or absence of at least one analyte in the fluid sample, wherein the first collection chamber is not in fluid communication with the second collection chamber.

12 Claims, 7 Drawing Sheets

(51) Int. Cl.
*G01N 1/18* (2006.01)
*G01N 1/02* (2006.01)

(52) U.S. Cl.
CPC .............. *B01L 3/5029* (2013.01); *G01N 1/18* (2013.01); *B01L 2200/141* (2013.01); *B01L 2300/021* (2013.01); *B01L 2300/042* (2013.01); *B01L 2300/0825* (2013.01); *B01L 2400/0478* (2013.01); *G01N 2001/028* (2013.01)

(56) References Cited

U.S. PATENT DOCUMENTS

| | | | |
|---|---|---|---|
| 4,632,961 A | 12/1986 | Valkirs et al. | |
| 4,717,656 A | 1/1988 | Swanljung | |
| 4,774,192 A | 9/1988 | Terminiello et al. | |
| 4,775,636 A | 10/1988 | Moeremans | |
| 4,810,630 A | 3/1989 | Craig et al. | |
| 4,817,632 A | 4/1989 | Schramm | |
| 4,826,759 A | 5/1989 | Guire et al. | |
| 4,853,335 A | 8/1989 | Olsen et al. | |
| 4,883,764 A | 11/1989 | Kloepfer | |
| 4,943,522 A | 7/1990 | Eisinger et al. | |
| 4,959,324 A | 9/1990 | Ramel et al. | |
| 4,963,325 A | 10/1990 | Lennon et al. | |
| 5,006,464 A | 4/1991 | Chu et al. | |
| 5,028,535 A | 7/1991 | Buechler et al. | |
| 5,071,746 A | 12/1991 | Wilk et al. | |
| 5,079,029 A | 1/1992 | Saunders | |
| 5,079,172 A | 1/1992 | Hari et al. | |
| 5,104,619 A | 4/1992 | DeCastro et al. | |
| 5,221,627 A | 6/1993 | Grigg et al. | |
| 5,244,815 A | 9/1993 | Guirguis | |
| 5,260,031 A | 11/1993 | Seymour | |
| 5,268,148 A | 12/1993 | Seymour | |
| 5,270,167 A | 12/1993 | Francouer | |
| 5,283,038 A | 2/1994 | Seymour | |
| 5,308,580 A | 5/1994 | Clark | |
| 5,342,645 A | 8/1994 | Eisele et al. | |
| 5,376,337 A | 12/1994 | Seymour | |
| 5,378,492 A | 1/1995 | Mashiko | |
| 5,380,492 A | 1/1995 | Seymour | |
| 5,393,496 A | 2/1995 | Seymour | |
| 5,416,000 A | 5/1995 | Allen et al. | |
| 5,441,698 A | 8/1995 | Norell | |
| 5,468,648 A | 11/1995 | Chandler | |
| 5,494,646 A | 2/1996 | Seymour | |
| 5,629,164 A | 5/1997 | Rivers | |
| 5,869,345 A | 2/1999 | Chandler | |
| 5,876,926 A | 3/1999 | Beecham | |
| 5,935,864 A | 8/1999 | Schramm et al. | |
| 6,352,863 B1 | 3/2002 | Guirguis | |
| 6,365,417 B1 | 4/2002 | Fleming et al. | |
| 6,766,817 B2 | 7/2004 | Da Silva | |
| 7,060,505 B2 | 6/2006 | Guirguis | |
| 7,927,560 B2 * | 4/2011 | Richard | B01L 3/502 422/401 |
| 7,927,562 B2 | 4/2011 | Wan et al. | |
| 9,198,641 B2 | 12/2015 | Slowey et al. | |
| 2002/0160538 A1 | 10/2002 | Guirguis | |
| 2004/0029261 A1 | 2/2004 | Oldfield | |
| 2004/0235192 A1 | 11/2004 | Guirguis | |
| 2005/0163660 A1 * | 7/2005 | Wang | B01L 3/502 422/417 |
| 2006/0000894 A1 | 1/2006 | Bonalle et al. | |
| 2007/0179436 A1 | 8/2007 | Braig et al. | |
| 2007/0239069 A1 | 10/2007 | Guirguis | |
| 2008/0194041 A1 | 8/2008 | Guirguis | |
| 2009/0306543 A1 | 12/2009 | Slowey et al. | |

FOREIGN PATENT DOCUMENTS

| | | |
|---|---|---|
| EP | 0440350 | 8/1991 |
| WO | 9216842 | 10/1992 |
| WO | 9306486 | 4/1993 |

OTHER PUBLICATIONS

Written Opinion of the International Searching Authority; International Application No. PCT/US18/15508; International Filing Date Jan. 26, 2018; 4 pages.

Cone et al., "Stability of Cocaine in Saliva", Clinical Chemistry, vol. 34(7), p. 1508, 1988.

Schramm et al.. "An Ultrafiltrate of Saliva Collected in Situ as a Biological Sample for Diagnostic Evaluation", Clinical Chemistry, vol. 37(1), p. 114-115, 1991.

Wolff et al., "Methadone in Saliva", Clinical Chemistry, vol. 37(7), p. 1297-1298, 1991.

Craig Medical Distribution, Inc., www.craigmedical.com/products.htm, printed Feb. 17, 2017.

* cited by examiner

DUAL SWAB FLUID SAMPLE COLLECTION FOR SPLIT SAMPLE TESTING AND FINGERPRINT IDENTIFICATION DEVICE

CROSS-REFERENCE TO RELATED APPLICATIONS

This application is a divisional application of U.S. non-provisional application Ser. No. 15/417,905, filed on Jan. 27, 2017.

BACKGROUND OF THE INVENTION

1. Field of the Invention

The present invention relates to substance collection and testing. More particularly, the present invention relates to a device that tests a fluid sample for the presence or absence of at least one analyte, secures a separate fluid sample for later confirmation, and provides positive identification of an individual associated with the sample. In another aspect, the present invention relates to a device for collecting a fluid sample.

2. Background

Drug and other analyte testing has become ubiquitous in modern society. In homes, doctors' offices, law enforcement vehicles and offices, athletic facilities, and the workplace, effective, inexpensive and reliable testing devices have been sought. There is also a growing need for devices to test bodily fluids for substances that may assist in the diagnosis or management of diseases and other medical conditions.

The marketplace responded and is now replete with many devices directed to the testing of blood, urine or saliva. However, these devices may require a series of tests involving the shifting of the fluid sample being tested to different containers and/or the removal of the fluid sample to distant locations. These devices may also require the test administrator to handle the test subject's bodily fluids, incurring a danger of disease exposure.

Once an initial test result has been obtained, further testing of the same fluid sample to confirm or refine the initial test result is often required. For a membrane test strip device, the fluid sample may not even be retained once the initial result is obtained, necessitating retention of a split sample. The need to retain a split sample incurs the risk that a sample could be lost, mislabeled, or contaminated.

Oftentimes, the chain of custody associated with a test sample imbues the results with doubt, as the fluid sample may become contaminated, misplaced or a different fluid sample may be substituted entirety. In many instances, identification of the test subject associated with the fluid sample is critically dispositive.

Prior art testing devices include those disclosed in U.S. Pat. Nos. 7,879,623 and 8,940,527, both entitled "Integrated Device for Analyte, Testing, Confirmation, and Donor Identity Verification" and both identifying Raouf A. Guirguis as the sole inventor. U.S. Pat. Nos. 7,879,623 and 8,940,527 are both hereby incorporated by reference. The patents disclose an apparatus for fluid sample collection and analyte testing, including a single sample receiving member and at least one membrane test strip, and optionally a sample retention member, fingerprint acquisition pad, and/or fluid collector. It also provides a fluid collection apparatus having an absorbent material, compression element, and closure element, and optionally a lid that allows the apparatus to be used in conjunction with a fluid container. Also provided are methods of collecting, testing, and retaining a fluid sample and verifying the identity of one or more individuals associated with the sample, such as the test subject, test administrator, and/or witnesses. The components for collecting, testing, and retaining a fluid sample are in fluid communication with the other components of the testing device.

There is also a growing need for devices directed to testing for contaminants that may be found in food or water, such as pollutants, allergens, and harmful microbes. In some instances, it may be desirable to retain a fluid sample for confirmation testing or further analysis, retain a split fluid sample of the original sample for confirmation testing or further analysis, or to provide positive identification of the test administrator.

The Department of Transportation's (DOT) rule, 49 C.F.R. Part 40, describes required procedures for conducting workplace drug and alcohol testing for the Federally regulated transportation industry. Within this rule, definitions for split sample and split sample collection are provided. Split specimen is defined as, in drug testing, a part of the urine specimen that is sent to a first laboratory and retained unopened, and which is transported to a second laboratory in the event that the employee requests that it be tested following a verified positive test of the primary specimen or a verified adulterated or substituted test result. Split specimen collection is defined as a collection in which the urine collected is divided into two separate specimen bottles, the primary specimen (Bottle A) and the split specimen (Bottle B).

Thus, a need exists in the industry to combine the simplicity of current membrane test strip technology with the ability to positively identify the test subject and/or the test administrator, as well as the capability to secure a split portion of the fluid sample with a single device for later confirmation, within a single device.

BRIEF SUMMARY OF THE INVENTION

According to one embodiment, the invention provides an apparatus for testing a fluid sample comprising: a sample receiving member having an opening for receiving a fluid sample, wherein the sample receiving member comprises at least a first and second sample collection chambers; a sample retention member, in fluid communication with the first sample collection chamber, to retain a portion of the fluid sample; and at least one test strip, in fluid communication with the second collection chamber, to indicate the presence or absence of at least one analyte in the fluid sample; wherein the first collection chamber is not in fluid communication with the second collection chamber.

According to one embodiment, the invention provides an apparatus for testing a fluid sample comprising: a sample receiving member having an opening for receiving a fluid sample; and a test cartridge member in fluid communication with the sample receiving member, to indicate the presence or absence of at least one analyte in the fluid sample; the test cartridge member comprising a test cartridge further comprising dual sets of back-to-back test strips including a front set of test strip slots and a back set of test strip slots.

BRIEF DESCRIPTION OF THE DRAWINGS

The above and other advantages of this invention will become more apparent by the following description of invention and the accompanying drawings.

DETAILED DESCRIPTION OF THE INVENTION

Analyte Screening

Figure 1:
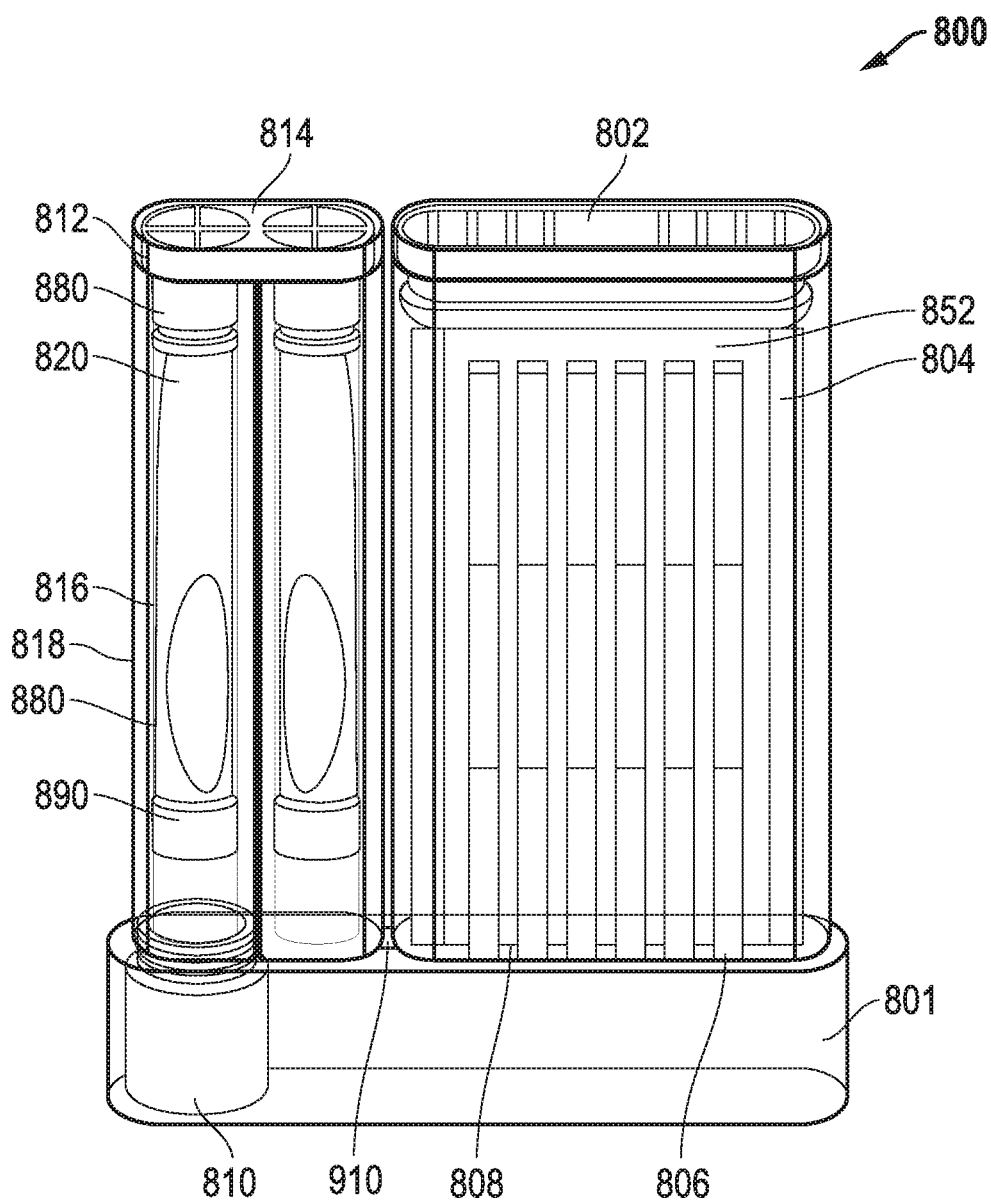
FIG. 1 depicts a perspective view of a fluid collection and analyte testing device in accordance with an embodiment of the present invention.

An embodiment of the present invention provides an analyte screening device which includes a rapid screening, lateral flow chromatographic immunoassay for the simultaneous, qualitative or quantitative detection of analytes in a fluid sample. For example, without limitation, the fluid sample may be saliva, urine, blood, mucus, water, or fluid extract of a solid or a semi-solid, for example stool or mucus or liquid biopsy. The fluid sample may also be an environmental sample, for example, without limitation, soil, dust, water, plant matter, insect, animal matter, or a fluid extract of any of the foregoing. The fluid sample may also be a food or beverage, for example, without limitation, a liquid beverage, a liquid-containing food, or a fluid extract of a solid, semi-solid or powdered food or beverage. The fluid sample may also contain genomic or proteomic material for testing and analysis.

An embodiment of the invention includes at least one membrane test strip, in fluid communication with a sample receiving member, able to indicate the presence or absence of at least one analyte above or below a threshold concentration in the fluid sample using a lateral flow chromatographic assay.

In an embodiment of the invention, the lateral flow chromatographic assay is a competitive assay, in which an analyte in the fluid sample competes with a competitor for binding with an anti-analyte antibody. For example, the anti-analyte antibody may be labeled, and the competitor may be immobilized in the test region of the membrane test strip. After the fluid sample reaches the dye region, it encounters the labeled anti-analyte antibody. If the analyte is present in the fluid sample above a predetermined threshold concentration, the analyte will saturate the binding sites of the labeled anti-analyte antibody; otherwise, some or the entire labeled anti-analyte antibody remains free to bind the competitor. As the fluid sample migrates along the membrane test strip by capillary action, it carries the labeled anti-analyte antibody along until it reaches the test region. The test region contains the immobilized competitor, which may be the analyte, fragments of the analyte, epitopes of the analyte, molecular mimics of the analyte, anti-idiotypic antibodies, or any other molecule able to compete with the analyte for binding to the anti-analyte antibody. If the analyte is present above the predetermined threshold concentration, the labeled anti-analyte antibody is saturated and does not bind the immobilized competitor, resulting in no signal in the test region; otherwise, the anti-analyte antibody is unsaturated and can bind to the competitor, resulting in a signal in the test region.

Thus, according to an embodiment of the invention employing a competitive assay, an analyte-negative fluid sample (containing lower than the predetermined concentration of the analyte) will generate a line in the test region due to capture of the labeled anti-analyte antibody, whereas an analyte-positive fluid specimen will not generate a colored line in the test region because the analyte in the fluid sample will saturate the labeled antibody and thus prevent its capture in the test region.

In an embodiment of the invention, the lateral flow chromatographic assay is a sandwich assay, in which the analyte must be present for the labeled anti-analyte antibodies to be captured in the test region. For example, the analyte antibody may be a labeled antibody, and a second anti-analyte antibody may be immobilized in the test region. For example, after the fluid sample reaches the dye region, it encounters the labeled anti-analyte antibody. If the analyte is present in the fluid sample, it will bind at least a fraction of the labeled anti-analyte antibody. As the fluid sample migrates along the membrane test strip by capillary action, it carries the labeled anti-analyte antibody along until it reaches the test region. The test region contains an immobilized anti-analyte antibody, which may be reactive against a different epitope of the analyte than the labeled anti-analyte antibody. If the analyte is present in the fluid sample, it forms a scaffold through which the labeled antibodies are immobilized in the test region. The fraction of the labeled antibodies captured in the test region is thus determined by the concentration of analyte in the fluid sample. If the analyte of interest is present above a predetermined threshold concentration, a sufficient fraction of the labeled antibodies are captured, resulting in a visible signal in the test region; otherwise, an insufficient fraction of the antibodies are captured and no signal is visible in the test region.

Thus, according to an embodiment of the invention employing a sandwich assay, an analyte-positive fluid specimen will generate a colored line in the test region of the membrane test strip due to the capture of the labeled antibody in the test region, whereas an analyte-negative fluid sample will not generate a fine in the test region due to failure to capture the labeled antibody.

Embodiments of the invention include a positive control to indicate that the assay has functioned properly and is complete. For example, the dye region may include a labeled control protein, including without limitation a labeled control antibody, and the control region of the membrane test strip may contain an immobilized control agent able to capture the labeled control protein, such as an antibody or a control analyte. The control region may be located distal to each test region on the membrane test strip, such that the fluid sample will encounter each test region before encountering the control region. The reaction of the labeled control protein with the immobilized control agent produces a colored line in the control region, indicating that a proper volume of the fluid sample has been added and membrane wicking has occurred, and the assay has worked properly.

An embodiment of the invention concurrently tests for multiple analytes, for example by employing membrane test strips capable of testing multiple analytes concurrently (for example, by containing multiple anti-analyte antibodies in the dye region and having multiple compatible test region), and/or by employing multiple membrane test strips within the same apparatus. An embodiment of the invention includes both membrane test strips that employ a competitive assay and a sandwich assay, for example on different membrane test strips within the device and/or on the same membrane test strip within the device.

Embodiments of the invention may provide quantitative determination of the concentration of an analyte that is present in the fluid sample. For example, the apparatus may include multiple membrane test strips having varying amounts of an anti-analyte antibody, resulting in varying analyte sensitivity, such that the concentration of the analyte is indicated by which of the membrane test strips show or fail to show a colored line in the test region.

Antibodies

An embodiment of the invention employs antibodies for the detection of analytes. The term "antibody" (Ab) as used herein includes monoclonal antibodies, polyclonal antibodies, multispecific antibodies (for example bispecific antibodies), and antibody fragments, so long as they exhibit the desired activity. The term "monoclonal antibody" as used herein refers to an antibody obtained from a population of substantially homogeneous antibodies, that is, the individual antibodies comprising the population are identical except for possible naturally occurring mutations that may be present in minor amounts.

The terms "labeled antibody" and "labeled control protein" refer to an antibody or protein that is conjugated directly or indirectly to a label. The label is a detectable compound or composition that may be detectable by itself, Including without limitation a dye, colloidal metal (including without limitation colloidal gold), radioisotope, or fluorescent compound, or, in the case of an enzymatic label, may catalyze chemical alteration of a substrate compound or composition which is detectable, or any combination of the foregoing.

Analytes

According to an embodiment of the invention, the apparatus includes a device for testing a fluid sample for the presence of analytes. The present invention contemplates testing for any analyte. Without limitation, analytes that may be tested for include drugs of abuse or their metabolites, analytes indicating the presence of an infectious agent or product of an infectious agent, allergen, pollutant, toxin, contaminant, analyte with diagnostic or medical value, antibody against any of the foregoing, and any combination thereof.

According to an embodiment of the invention, analytes that may be tested for include drugs of abuse and their metabolites, including without limitation 7-acetaminoclonazepam, alkyl nitrites, alpha-hydroxyalprazolam, alprazolam, 2-amino-2'-chloro-5-nitrobenzophenone, 7-aminoclonazepam, 7-aminonitrazepam, amitriptyline, amobarbital, amoxapine, amphetamine, anabolid steroids, androgen, androstadienone, aprobarbital, atropine, barbiturates, benzodiazepines, benzoylecgonine, benzylpiperazine, boldenone undecylenate, 4-bromo-2,5-dimethoxyphenethylamine, bovine growth hormone, butabarbital, butalbital, butripryline, 4-chlordehydromethyltesto sterone, chloroform, clomipramine, clonazepam, clostebol, cocaethylene, cocaine, codeine, codeine-6-glucuronide, cotinine, dehydroepiandrosterone, desipramine, desmethyldiazepam, desoxymethyltestosterone, dexmethylphenidate, dextroamphetamine, dextromethorphan, dextropropoxyphene, dextrorphan, 2,5-diamino-2'-chlorobenzophenone, diamorphine, diazepam, dibenzepin, dihydrotestosterone, dimenhydrinate, 2,5-dimethoxy-4-(n)-propylthiophenethylamine, 2,5-dimethoxy-4-ethylphenethylamine, 2,5-dimethoxy-4-iodophenethylamine, dimethyl ether, dimethyltryptamine, dimethyltryptamine, diphenhydramine hydrochloride, dosulepin hydrochloride, dothiepin hydrochloride, doxepin, drostanolone, ecgonine, ecgonine methyl ester, ephedrine, ergine, estren, 5-estrogen, ethyl-5-(1'-methyl-3'-carboxypropyl)-2-thiobarbituric acid, 5-ethyl-5-(1-'-methyl-3'-hydroxybutyl)-2-thiobarbituric acid, ethylestrenol, ethylphenidate, fentanyl, flunitrazepam, fluoxymesterone, furazabol, gamma-hydroxybutyrate, 1-(beta-D-glucopyranosyl) amobarbital, growth hormone, heroine, hexabarbital, human chorionic gonadotropin, human growth hormone, hydrocodone, hydromorphone, (+)-3-hydroxy-N-methylmorphinan, 3-hydroxy clonazepam, 11-hydroxy-tetrahydrocannabinol (11-hydroxy-THC), 3'-hydroxyamobarbital, p-hydroxyamphetamine, p-hydroxynorophedrine, imipramine, iprindole, kava, katamine, levomethylphenidate, iofepramine, lorazepam, lorazepam-glucuronide, lysergic acid diethylamide, meperidine, mescaline, mestanolone, mesterolone, metachlorophenylpiperazine, methadone, methamphetamine, methandrostenolone, methcathinone, 3,4-methylenedioxy amphetamine, methanolone, methanolone enanthate, methylenedioxymethamphelamine (ecstacy), methylphenidate, methylphenobarbital, methyl testosterone, mibolerone, (+)-3-morphinan, morphine, nandrolone, nicotine, nitrazepam, N-methyl-diethanciamine, norbolethone, norcodeine, norethandrolone, norketamine, nortriptyline, opiates, opipramol, opium, oxabolone opionate, oxandrolone, oxazepam, oxycodone, oxymetholone, oxymorphone, pentobarbital, phencyclidine, phenethylamines, phenobarbital, 4-phenyl-4-(1-piperidinyl)-cyclohexanol, 1-phenyl-1-cyclohexene, phenylacetone, 5-[N-(1-phenylcyclohexyl)]-aminopentanoic acid, 1-(1-phenylcyclohexyl)-4-hydroxypiperidine, piperidine, protriptyline, psilocin, psilocybin, quinbolone, salvinorin A, scopolamine, secobarbital, sodium thiopental, stanozolol, telbutal, temazepam, testosterone, testosterone proprionate, tetrahydrocannabinol (THC), THC-COOH, tetrahydrogestrinone, toluene, trenbolone, tricyclic antidepressant, 3-trifluoromethylphenylpiperazine, trimipramine, tryptamines, or any combination thereof. The minimum concentration level at which the presence of any particular drug or metabolite is detached may be determined by various industry minimum standards, such as, for example, the National Institute on Drug Abuse (NIDA), the Substance Abuse & Mental Health Services Administration (SAMHSA), and the World Health Organization (WHO).

According to an embodiment of the invention, analytes that may be tested for include infectious agent or the products of an infectious agent, including without limitation *Acanthamoeba*, aflatoxin, alimentary mycotoxlcoses, altertoxin, amoeba, *Anisakis, Ascaris lumbricoides, Bacillus arthracis, Bacillus cereus* or its toxin, bacteria, bovine spongiform encephalopathy prioris, *Brucella*, Caliciviridae, *Calymmatobacterium granulomatis, Campylobacter,*

*Campylobacter jejuni, Candida, Candida albicans, Cephalosporium, Chlamydia trachomatis*, chronic wasting disease prions, Citrinin, *Clostridium botulinum* or its toxin, *Clostridium perfringens, Corynebacterium ulcerans, Coxiella burnetil*, Creutzieldt-Jakob disease prions, *Cryptococcus neoformans, Cryptosporidium, Cryptosporidium parvum* Cycloplazonic acid, *Cyclospera cayetanensis*, Cytochaiasin, Cytomegalovirus, Diphyilobothrium, *Escherichia Coli*, Ebola, endotoxin, Entamceba histolytica, Enterovirus, Ergopeptine alkaloid, Ergot alkaloid, Ergotamine, *Escherichia coli* 0157, *Eustrongylides, Fasciola hepatica*, fatal familial insomnia prions, flatworm, *Francisella tularensis*, Fumitremorgen B.sub.1 Fumonisin, *Fusarium*, Fusarochromanone, genital warts, Gerstmann-Straussler-Scheinker syndrome prions, *Giardia, Giardia lamblia*, Granuloma inguinale, H7 enterohemorrhagic, *Haemophilus ducreyl, Helicobacter pylori*, Hepatitis, Hepatitis A, Hepatitis B, Hepatitis C, Hepatitis D, Hepatitis E, Hepatitis E, herpes simplex virus, *Histoplasma capsulatum*, HIV, HIV-1, HIV-2, human papillomavirus, influenza, Kaposi's sarcoma-associated herpesvirus, Kojic acid, kuru prions, *Listeria monocytogenes*, Lolitrem alkaloids, marburg virus, Methicillin-resistant *Staphylococcus aureus* or its toxin, molluscum, Moniliformin, mononucleosis, mycobacteria, *Mycobacterium tuberculosis, Mycoplasma, Mycoplasma hominis*, Mycotoxins, *Myrothecium, Nanophyetus, Neisseria* gonorrhosae, nematode, Nivalenol, Norovirus, Oohratoxins, Oosporeine, parasite, Patulin, Paxilline, Penitrem A, Phomopsins, *Plasmodium*, Platyhelminthes, *Plesiomonas shigelloides, Penumococcus, Pneumocystis jirovecii*, prions, protozoa, rhinovirus, Rotavirus, *Salmonella, Sarcocystis hominis, Sarcocystis sulhominis*, scraple prions, sexually transmitted disease, *Shigella, Shigella*, Sporidesmin A, Stachybotrys, *Staphylococcus aureus* or its toxin, Sterigmatocystin, *Streptococcus, Streptococcus pneumoniae, Streptococcus pyogenes, Taenia saginata, Taenia solium*, tapeworm, *Tenia solium*, Tinea, *Toxoplasma gondii, Tremorgenic mycotoxins, Treponema palidum, Trichinella spiralis, Trichoderma, Trichomonas vaginalis*, Trichothecene, *Trichuris trichlura, Typanosoma cruzi, Ureaplasma urealyticum*, Verrucosidin, Varruculogen, *Vibrio cholerae* non-O1, *Vibrio cholerae* O1, *Vibrio-parahaemolyticus, Vibrio vulnificus*, viruses, yeast infections, *Yersinia enterocolitica, Yersinia pseudotuberculosis*, Zearalenois, Zearalenone, antibodies against any of the foregoing, or any combination thereof.

According to an embodiment of the invention, the analytes to be tested for include allergens, including without limitation *aesculus*, aider, almonds, animal products, arternisia vulgaris, beans, bet sting venom, birch, calyx, cat dander, celeriac, celery, *Chenopodium album*, cockroach, corn, dander, dong dander, drugs, dust mite excretion, egg albumen, eggs, Fei d 1 protein, fruit, fur, grass, hazel, hornbeam, insect stings, latex, legumes, local anaesthetics, maize, metal, milk, mold spores, mosquito saliva, mouse dander, nettle, olea, peanuts, peas, pecans, penicillin, Plant pollens, plantago, platanus, poplar, pumpkin, ragweed, rat dander, ryegrass, salicylates, seafood, sesame, sorrel, soy, soybeans, sulfonamides, tilia, timothy-grass, tree nuts, trees, wasp sting venom, weeds, wheat, willow, antibodies against any of the foregoing, or any combination thereof.

According to an embodiment of the invention, the analytes to be tested for include pollutants, toxins, and contaminants, including without limitation 1,2-Dibromoethane, acrylamide, aldehydes, arsenic, artificial growth hormone, asbestos, benzene, benzopyrene, carcinogens, dichloro-diphenyl-trichloroethane, formaldehyde, kepone, lead, mercury, methylmercury, nitrosamines, N-nitroso-N-methylurea, organochlorine insecticides, pesticides, polychlorinated biphenyls, polychlorinated dibenzofurans, polychlorinated dibenzo-p-dloxins, recombinant bovine growth hormone, recombinant bovine somatotropin, toluene, vinyl chloride, antibodies against any of the foregoing, or any combination thereof.

According to an embodiment of the invention, the analytes to be tested for include analytes with diagnostic or medical value, including without limitation acid phosphatase, active-B 12, AFP, Alanine Aminotransferase, Alanine Aminotransferase, Albumin, Albumin BCG, Albumin BCP, Alkaline Phosphatase, Alpha-1 Antitrypsin, Alpha-1 Glycoprotein, Amikacin, Ammonia, Amylase, Anti-CCP, Anti-Tg, Anti-TPO, Apolipoprotein A1, Apolipoprotein B, ASO, Asparate Aminotransferase, Aspartate Aminotransferase, B12, Beta2 Microglobulin, Beta2 Microglobulin, BNP, CA 125, CA 125 II, CA 15-3, CA 19-9 XR, Calcium, Carbamazepine, Carbon Dioxide, CEA, Ceruloplasmin, Cholesterol, CK-MB, Complement C3, Complement C4, Cortisol, C-Peptide, C-Reactive Protein, Creatine Kinase, Creatinine, CRP Vario, Cyclosporine, Cyclosporine and Metabolite-Whole Blood, Cyclosporine Monoclonal-Whole Blood, D-Dimer, DHEA-S, Digitoxin, Digoxin, Digoxin, Digoxin II, Digoxin III, Direct Billirubin, Direct LDL, Estradiol, Ferritin, FLM II, Folate, Free Carbamazepine, Free Phenytoin, Free PSA, Free T3, Free T4, Free Valproic acid, FSH, Gamma-Glutamyl Transferase, Gentamicin, Glucose, Glycated Hemoglobin, Haptoglobin, hCG, Hemoglobin, Homocysteine, ICT CI-, IGFBP-1, Immunoglobulin, Immunoglobulin A, Immunoglobulin E, immunoglobulin G, Immunoglobulin M, Insulin, Intact PTH, Iron, K+, Kappa Light Chain, Lactate Dehyrogenase, Lactic acid, Lambda Light Chain, LH, Lidocaine, Lipase, Lithium, Lp, magnesium, metabolites, Methotrexate II, Microalbumin, MPO, Myoglobin, Na+, N-Acetyl-procainamide, neonatal Billirubin, NGAL, P-Amylase, Pepsinogen I, Pepsinogen II, Phenobarbital, Phenytoin, Phosphorus, Prealbumin Procainamide, Progesterone, Prolactin, Quinidine, Rheumatoid Factor, SHBG, Sirollmus, STAT CK-MB, T4, Tacrolimus, Tacrolimus II, Testosterone, Tg, Theophylline, Theophylline II, TIBC, TIMP-1, Tobramycin, Total Billirubin, Total Estriol, Total Protein, Total PSA, Total T3, Total T4, Transferrin, Triglycerides, Troponin-I, Troponin-I ADV, TSH, T-Uptake, UIBC, Ultra HDL, Urea Nitrogen, Uric Acid, Urine/CSF Protein, Valproic Acid, Vancomycin, Vancomycin II, Vitamin D, antibodies against any of the foregoing, or any combination thereof.

Receiving Member

According to an embodiment or the invention, the apparatus includes a receiving member, having an opening to receive a fluid sample, For example, the receiving member may be dimensioned to receive a fluid collector. In an embodiment of the invention, the receiving member may be in fluid communication with other components of the apparatus, for example at least one membrane test strip, sample retention member, and/or an Immunoassay-based fingerprint acquisition pad, through channels, for example tubes, piping, channels molded or carved into the apparatus, or any other suitable structure, made of any suitable material, for example plastic, ceramic, metal, glass, wood, rubber, polymer, fiber-reinforced polymer, or any combination thereof.

According to an embodiment of the invention, the channel or channels providing fluid communication between the components may have differing flow resistance, for example having channels, channel segments, or openings, that are narrower, wider, longer, or shorter than others, and/or having fluid paths with varying amounts of vertical rise or drop, such that the fluid channels within the device have varying degrees of flow resistance. For example, the channel that provides the fluid communication of the sample receiving member with the at least one membrane test strip may have greater flow resistance than the at least one channel that provides the fluid communication of the sample receiving member with the sample retention member, to ensure that a portion of the fluid sample is collected in the sample retention member.

In an embodiment of the invention, a single channel having multiple openings may connect the receiving member to each of the components of the apparatus with which it is in fluid communication, for example the at least one membrane test strip, sample retention member, and/or immunoassay-based fingerprint acquisition pad.

In an embodiment of the invention, the receiving member may include two or more chambers for receipt of a multi-pronged fluid collector, including but not limited to a dual-swab fluid collector. Components of the apparatus may be solely connected to one of the multiple chambers. For example, in a two chamber embodiment, one chamber may be solely connected to a sample retention member to ensure that a portion of the fluid sample is collected and stored without interaction of the other components of the apparatus.

An embodiment of the invention may accommodate fluids of varying viscosity, for example water, saliva, urine, blood, and liquids associated with genomics and proteomics. Generally, this is accomplished by varying the diameter of the channel or channels that provide the fluid communication of the sample receiving member with the other components of the apparatus, for example providing a wider channel diameter to accommodate a more viscous fluid.

In an embodiment of the invention, a channel dimensioned to be compatible with a fluid having the viscosity of water provides the fluid communication of the sample receiving member with the at least one membrane test strip and at least one channel dimensioned to be compatible with a fluid having the viscosity of water provides the fluid communication of the sample receiving member with the sample retention member.

In an embodiment of the invention, a channel dimensioned to be compatible with a fluid having the viscosity of urine provides the fluid communication of the sample receiving member with the at least one membrane test strip and at least one channel dimensioned to be compatible with a fluid having the viscosity of urine provides the fluid communication of the sample receiving member with the sample retention member.

In an embodiment of the invention, a channel dimensioned to be compatible with a fluid having the viscosity of saliva provides the fluid communication of the sample receiving member with the at least one membrane test strip and at least one channel dimensioned to be compatible with a fluid having the viscosity of saliva provides the fluid communication of the sample receiving member with the sample retention member.

In an embodiment of the invention, a channel dimensioned to be compatible with a fluid having the viscosity of blood provides the fluid communication of the sample receiving member with the at least one membrane test strip and at least one channel dimensioned to be compatible with a fluid having the viscosity of blood provides the fluid communication of the sample receiving member with the sample retention member. In an embodiment of the invention, a channel dimensioned to be compatible with a fluid having the viscosity of mucus provides the fluid communication of the sample receiving member with the at least one membrane test strip and at least one channel dimensioned to be compatible with a fluid having the viscosity of mucus provides the fluid communication of the sample receiving member with the sample retention member.

In an embodiment of the invention, a channel dimensioned to be compatible with a fluid having the viscosity of liquid associated with cell separation provides the fluid communication of the sample receiving member with the at least one membrane test strip and at least one channel dimensioned to be compatible with a fluid having the viscosity of liquid associated with cell separation provides the fluid communication of the sample receiving member with the sample retention member.

In an embodiment of the invention, a channel dimensioned to be compatible with a fluid having the viscosity of liquid biopsy, such as proteomics or genomics, provides the fluid communication of the sample receiving member with the at least one membrane test strip and at least one channel dimensioned to be compatible with a fluid having the viscosity of liquid biopsy provides the fluid communication of the sample receiving member with the sample retention member. Proteomics is the study of proteins. Genomics is a branch of molecular biology concerned with the structure, function, evolution, and mapping of genomes.

In an embodiment of the invention, the receiving member may have an inner surface, for example a lower surface, that an absorbent material, such as an absorbent material present in a fluid collector, may be compressed against, thereby expelling the fluid sample from the absorbent material. For example, the absorbent material may be compressed directly between a compression member present on the fluid collector and the lower surface of the receiving member or the receiving member may provide structural support to facilitate compression of the absorbent material between a compression member and the housing that at least partially surrounds the absorbent material.

Sample Retention Member

According to an embodiment of the invention, the apparatus includes a sample retention member. The sample retention member may be used to securely contain a portion of the fluid sample, such as a split sample. The retained portion of the fluid sample may be used for further testing, for example for confirmation of a test result obtained using a membrane test strip, or to test for the presence or absence of other analytes in the fluid sample. The retained portion of the fluid sample may also be used for confirmation of the test subject's identity through analysis of a distinguishing feature thereof, including without limitation DNA, cells, proteomics, metals, and liquid biopsy.

According to one embodiment of the invention, the sample retention member includes an absorbent material, for example a pad or sponge, or made of woven or non-woven fibrous or fabric-like material, for example cellulose or a cellulose derivative, cotton, hydrophilic foam, wood pulp, polyvinyl alcohol fibers, or any combination thereof. The sample retention member may include an absorbent material that is part of the sample collection apparatus. The absorbent material may be surrounded by a barrier, such as a liquid-impermeable material, including without limitation plastic, ceramic, metal, glass, wood, rubber, polymer, fiber-reinforced polymer, or any combination thereof, to prevent the retained sample from leaking or evaporating. In an embodiment of the invention, the absorbent material may be removably attached to the apparatus to facilitate retrieval of the retained fluid sample. In an embodiment of the invention, the absorbent material may be accessed using a needle, for example by piercing a barrier surrounding the absorbent material. The retained sample may then be removed, for example, into a syringe attached to a needle, by means of withdrawal of the syringe to create suction.

According to an embodiment of the invention, the sample retention member includes a storage container defining a volume for storage of the fluid sample. In one embodiment of the invention, the sample retention member may be a vial made from a breakable or nearly unbreakable material, including without limitation glass, plastic, ceramic, metal, metal foil, wood, rubber, polymer, fiber-reinforced polymer, or any combination thereof. In an embodiment of the invention, the storage container may be accessed using a needle to pierce the wall of the storage container. For example, the storage container may include a pierceable member, such as a region of decreased wall thickness, and/or made of a soft, pierceable, or breakable material, including without limitation plastic, ceramic, metal, glass, metal foil, wood, rubber, polymer, fiber-reinforced polymer, or any combination thereof, that may be pierced. The retained sample may then be removed, for example, into a syringe attached to a needle, by means of withdrawal of the syringe to create suction. In an embodiment of the invention, the storage container may be removably attached to the apparatus, including without limitation, through a line of weakness that may allow the storage container to be broken free form the apparatus, through a threaded connection mechanism between the sample retention member and the fluid sample testing device, or through a twisting lock connection mechanism between the sample retention member and the fluid sample testing device.

According to an embodiment of the invention, the removable sample retention member may be linked to or coded consistently with the fluid sample testing device, including but not limited to, identical or related identification or serial numbers on both the sample retention member and the fluid sample testing device, identical or related bar code information on both the sample retention member and the fluid sample testing device, and the inclusion of radio frequency identification devices (RFID) on the sample retention member or the sample retention member and the fluid sample testing device. RFID incorporates the use of electromagnetic or electrostatic coupling in the radio frequency (RF) portion of the electromagnetic spectrum uniquely identify an object; such unique identification information may be information specific to the sample provider or information unique to the fluid sample testing device.

According to an embodiment of the invention, the sample retention member contains substances that facilitate a further use of the sample, including without limitation preservatives of stabilizers able to preserve sample integrity, for example substances able to inhibit microbial growth, kill microbes, prevent sample leakage, prevent sample evaporation, inhibit chemical or enzymatic degradation of substances in the sample, support survival of cells or other microbes in the sample, or any combination thereof.

According to an embodiment of the invention, the sample retention member may be bonded to a fingerprint acquisition pad. For example, such a bond may provide a safeguard against dissociation of the retained sample from the fingerprint.

According to an embodiment of the invention, the sample retention member may be in fluid contact solely with the sample receiving member and may not have any fluid contact with any other component of the apparatus.

The retained fluid sample may be used for further confirmation testing, including without limitation gas chromatography, liquid chromatography, mass spectrometry, liquid or gas chromatography with tandem mass spectrometry, polymerase chain reaction, DNA sequencing, Enzyme-Linked ImmunoSorbent Assay, Western Blotting, culturing for growth, or any combination thereof, using the retained fluid sample.

Fluid Collector

An embodiment of the apparatus comprises a fluid collector for collecting a fluid sample. The present invention contemplates collecting a sample from a specific subject, such as a human subject, or testing environmental samples, such as testing air, water, soil, or some other substance, or a food or beverage, or a liquid extract of any of the foregoing for example, without limitation. The fluid collector is operative associated with the apparatus. The fluid collector may be removably associated with the apparatus/affixed to the apparatus, or comprise multiple units of which one or more is affixed or removably associated with the apparatus.

In an embodiment of the invention, the fluid collector includes an absorbent material or swab capable of absorbing a desired quantity of a fluid sample. The absorbent material may be made of any suitable material known to a person in the art, for example, without limitation, a pad or sponge, or woven or non-woven fibrous or fabric-like material, including without limitation cellulose or a cellulose derivative, cotton, hydrophilic foam, wood pulp, polyvinyl alcohol fibers, or any combination thereof. In an embodiment of the invention, the fluid collector includes a compression member, able to compress the absorbent material, that may be used to expel air from the absorbent material prior to collection of the fluid sample and/or encourage the fluid sample to flow into the absorbent material by creating suction as the compressed absorbent material returns to the uncompressed state. A compression member may also be used, for example, to compress the absorbent material and expel a fluid sample contained therein.

In one embodiment of the invention, the fluid collector includes multiple collection swabs. For example, a two-prong fluid collector with dual swabs may be implemented to collect the sample. In one embodiment, each swab of a multi-swab fluid collector may be selected based upon the specific swab collection characteristics. For example, in a dual-swab fluid collector, each swab may contain a material to assist in the collection of different samples such as the collection of different cell material.

A sufficiency indicator on the collector is contemplated. For example without limitation, a color indicator may either appear or disappear when a sufficient sample has been collected, for example when a sufficient volume has been absorbed to reach the location in the absorbent material where the sufficiency indicator is disposed. According to an embodiment of the invention, the sufficiency indicator may be operatively associated with the absorbent material and may protected from direct contact with the source of the fluid sample by a barrier, such as a transparent barrier, for example plastic or glass, such that the fluid sample will only reach the sufficiency indicator by passing into the absorbent material.

The sufficiency indicator color may be in the shape of a word or symbol that appears or disappears when a sufficient sample has been collected. For example, the sufficiency indicator may a diffusible dye, wherein dilution of the dye by the fluid sample causes a color to disappear, indicating that a sample of sufficient volume has been collected. In an embodiment of the invention, a combination of a non-diffusible and diffusible dye may be used together, such that the non-diffusible dye remains and provides an informative message when the diffusible dye disappears, for example the diffusible dye may form the letters "in" in the word "insufficient" such that the non-diffusible dye remains and forms the word "sufficient" when a sufficient sample has been collected.

The sufficiency indicator may be a pH-sensitive substance that changes color when the sample is encountered. For example, multiple pH sensitive indicators responding to different pH values may be preset, such that a color change is observed whether the sample is acidic, basic, or neutral. According to an embodiment of the invention, a pH-changing substance, such as an acid or base, may be disposed within the absorbent material, such that the sample will be of the correct pH to elicit the desired color change in the sufficiency indicator.

A closure member may be used. The closure member is capable of sealing the open end of a sample receiving member when the fluid collector is inserted into the open end of a sample receiving member. For example, the closure member may be dimensioned to fit closely in the opening in the open end of the receiving member, and the closure member or the open end of the receiving member may include a compressible material, including without limitation natural rubber such as vulcanized rubber, synthetic rubber such as neoprene or nitrite rubber, plastic, ceramic, or any combination thereof, disposed at the interface between the closure member and the opening in the open end of the sample receiving member, capable of creating a seal, such as an airtight or a watertight seal, when the sample receiving member receives the fluid collector.

After the fluid collector has been inserted into the sample receiving member, a device for securing the fluid collector within the sample receiving member is contemplated. The means for securing may prevent removal of the fluid collector from the sample receiving member after it has been inserted therein. The means for securing the fluid collector within the sample receiving member may include at least one projection extending from the fluid collector that cooperates with the at least one projection located on the inner surface of the sample receiving member, where such projections may include for example at least one locking tab and/or at least one annular ring. According to an embodiment of the invention, a closure member on the fluid collector may form a sufficiently secure closure as to constitute means for securing the fluid collector within the sample receiving member.

The sample receiving member may also include a tamper-evident seal, such that attempting to tamper with the contents of the apparatus will result in a visual indicator, for example by tears or breakage visible in an imprinted seal, for example tape or adhesive-backed foil having characters, symbols or a signature on a surface. Such a tamper-evident seal may be placed on the apparatus before its use, to create a visual confirmation that the intents of the apparatus have not been altered via the open end of the receiving member prior to testing, or after its use, to create a visual confirmation that the contents of the apparatus have not been altered via the open end of the receiving member subsequent to testing. According to an embodiment of the invention, the means for securing the fluid collector within the sample receiving member may constitute a tamper evident seal, in that attempted removal of the fluid collector from the sample receiving member after it has been inserted therein may result in visible damage to the apparatus.

According to an embodiment of the invention, the fluid collector includes a handle, for example made of wood, plastic, ceramic, or metal, and disposed, for example, at the end distal to the absorbent material. The handle may be removably attached, for example through an interference fit, adhesive, glue, or epoxy, that breaks or separates when the handle is twisted and/or pulled, or by a structure that allows the handle to be broken away, for example, a line of weakness.

The fluid collector may include a housing that at least partially surrounds the absorbent material. The housing may have multiple openings to allow the fluid sample to be absorbed by and expressed from the absorbent material. The openings in the housing may contain filtration members able to strain particulates from the fluid sample, resulting in reduction of the number of particulates that enter the absorbent material. The fluid collector may include a compression member able to compress the absorbent material against the housing. For example, the housing may be slideably coupled to a compression member with the absorbent material disposed between the compression member and an inner surface of the housing, such that the absorbent material may be compressed by movement of the compression member towards an inner surface of the housing. An embodiment of the invention includes means for securing the absorbent material in the compressed state, including without limitation cooperating threads, projections, and/or grooves operatively associated with the compression member and the housing. The absorbent material may be released from the compressed state before, concurrently with, or after encounter with the fluid sample, facilitating entry of the fluid sample into the absorbent material as the absorbent material returns to the relaxed state, creating suction. For example, the absorbent material may be operatively associated with a spring, such that compression of the absorbent material results in compression of the spring, and when compression is released the spring assists return of the absorbent material to the uncompressed state.

In an embodiment of the invention, the fluid collector is operatively associated with the lid of a fluid container including without limitation a urine cup. For example, the absorbent material may be disposed on the inner side of the lid, such that attachment of the lid to the fluid container results in contact between the absorbent material and a fluid sample. In certain embodiments of the invention, a portion of the fluid collector including the lid may be removably associated with a portion of the fluid collector including the absorbent material, allowing the absorbent material to be separated from the lid. The operative association of the fluid collector with the lid may include means for arresting the rotation of part of the fluid collector relative to the lid, including without limitation cooperating projections present on one member and grooves or slots present on the other member, for example to facilitate release of means by which the absorbent material is fixed in the compressed state.

Saliva Producing Substances

Use of a saliva producing substance is contemplated by the present invention. Saliva producing substances elicit or increase saliva production in the test subject. For example, without limitation, the saliva producing substance may sugars, salts, acids, or any combination thereof. In an embodiment of the invention, the saliva producing substance may be associated with a fluid collector, for example located on or in the absorbent material or the housing. In an embodiment of the invention, the saliva producing substance may be separated from the fluid collector, for example in the form of a gum, candy, or powder, for administration to the test subject before, during or after the fluid collector is inserted into the test subject's mouth.

For example, without limitation, the sugar may be a monosaccharide, a disaccharide, a trisaccharide, an oligosaccharide, a polysaccharide, acarbose, allose, altrose, amylose, arabinose, calibiose, cyclodextrin, alph-cyclodextrin, beta-cyclodextrin, gamma-cyclodextrin, deoxyglucose, dextrin, dihydroxyacetone, erythrose, erythrulose, ficoli, fructo-oligosaccharides, fructose, galacto-oligosaccharides, galactose, gentiobiose, glucoasmine, glucose, glyceraldehyde, glycogen, gulosse, idose, inositol, inulin, isomaltose, lactose, lyxose, maltose, maltosyl-cyclodextrin, malt-trifose, mannan-oligosaccharides, mannoheptulose, marinose, melexltose, monnitol, psiccae, raffinose, ribitol, ribose, ribulose, sedoheptulose, sorbitol, sorbose, sucrose, tagatose, talose, threose, trehalose, xylose, xylulose, or any combination thereof.

For example, without limitation, the salt may an inorganic salt, organic salt, acid salt, alkali salt, neutral salt, or amino acid salt, or any combination thereof. The salt may include a cation and an anion, for example without limitation thereto, the cation may be aluminum, ammonium, barium, beryilium, calcium, cesiu, chromium(II), chromium(III), chromium(IV), cobalt(II), cobalt(III), copper(I), copper(II), copper(III), gallium, helium, hydrogen, hydronium, iron(II), iron(III), lead(II), lead(IV), lithium, magnesium, manganese (II), manganese(III), manganese(IV), manganese(VII), nickel(II), nickel(III), nitronium, potassium, pyridinium, silver, sodium, strontium, tin(II), tin(IV), zinc, or any combination thereof, and an anion may be acetate, amide, tartrate, borate, bromate, bomide, carbonate, chlorate, chloride, chlorile, chromate, citrate, cyanate, dichormate, dihydrogen phosphate, fluide, formate, glutamate, hydride, hydrogen carbonate, hydrogen oxalate, hydrogen phosphate, hydrogen sulfate, hydrogen sulfite, hydroxide, hypobromite, hypochlorite, iodate, iodide, nitrate, nitride, nitrite, oxalate, oxide, perchlorate, permanganate, peroxide, phosphate, phosphide, phosphite, pyrophosphate, sulfate, sulfide, sulfite, telluride, thiocyanate, thiosulfate, or any combination thereof. For example, according to an embodiment of the invention, the salt may be sodium chloride or potassium chloride.

The acid may be any suitable acid known to a person skilled in the art, for example acetic acid, acrylic acid, adipic acid, alginic acid, alkanesulfonic acid, amino acid, asorbic acid, benzoic acid, boric acid, butyric acid, carbonic acid, carboxylic acid, citrio acid, fattys acid, folic acid, formic acid, fumaric acid, gluconic acid, hdyriodic acid, hydrobromic acid, hydrochloric acid, hydroquinosulfonic acid, isoascorbic acid, lactic acid, maleic acid, malio acid, malonic acid, methanesulfonic acid, nitric acid, oxalic acid, p-toluenesulfonic acid, para-bromophenylsulfonic acid, phosphoric acid, propionic acid, salicyclic acid, stearic acid, succinic acid, sulfuric acid, tannic acid, tartaric acid, thioglycolic acid, toluenesulfonic acid, uric acid, or any combination thereof.

Fingerprint Identification

An embodiment of the present invention includes a fingerprint pad to provide identification of an individual associated with the test, such as the test subject, test administrator, and/or one or more witnesses. The fingerprint pad may employ any suitable fingerprinting methodology, for example, without limitation, ink-based, immunoassay-based, electronic, semi-inkless, or inkless. In an embodiment of the invention, the fingerprint pad may be able to collect multiple fingerprints, for example having multiple fingerprint pads, having one fingerprint pad of sufficient size to accommodate multiple fingerprints, or having an electronic fingerprint pad.

The fingerprint pad may be an ink-based fingerprint pad. An embodiment of the invention includes a dispenser able to dispense an ink that can elicit a signal in the ink-based fingerprint pad. The fingerprint pad may also be inkless or semi-inkless, for example requiring no ink or compatible with an activator that appears transparent on the subject's skin, is readily cleaned off the subject's skin, or readily disappears, for example, when the subject's hands are rubbed together. According to an embodiment of the invention, the inkless fingerprint pad may be immunoassay-based, for example as described within U.S. Pat. No. 6,352,663 to Raouf A. Guirguis, issued Mar. 5, 2002 (the "'863 patent"), and U.S. Pat. No. 5,244,815 to Raouf A. Guirguis, issued Sep. 14, 1993 (the "'815 patent"), which are incorporated herein by reference in their entirety. The immunoassay-based fingerprint pad may or may not be in fluid communication with a sample receiving member. Other embodiments of the invention may incorporate various features of the embodiments disclosed within the '863 and '815 patents. In embodiment of the invention having an inkless or semi-inkless fingerprint pad that requires an activator to elicit a signal, the apparatus may also include a dispenser to dispense the activator. According to an embodiment of the invention, the fingerprint pad may have a surface, such as an absorbent or adhesive surface, able to gather sweat, oils, and/or skin cells when a finger is pressed against it, that may require further processing to permit clear visualization of the fingerprint.

According to an embodiment of the invention, an inkless fingerprint pad may be an electronic fingerprint pad, including without limitation an optical scan fingerprint reader or a solid-state fingerprint reader. An embodiment of the invention includes a memory element, including without limitation volatile or non-volatile memory, for example a hard disk, floppy disk, magnetic tape, optical disk, flash memory, holographic memory, EEPROM, RAM, DRAM, SDRAM, or SRAM coupled to the fingerprint pad for storage of one or more fingerprints. According to an embodiment of the invention, the electronic fingerprint pads may have electrically charged surface elements, wherein portions of the surface are electrically discharged upon contact with the finger surface, such as the ridges of the finger surface, such that the fingerprint is recorded in the pattern of discharged elements, whereby the fingerprint pattern may be stably stored within the surface for a time after it is created until it is read, for example through connection of the apparatus with an external device, including without limitation a base station. An embodiment of the invention include means of transmission of the captured fingerprint, for example to an external device or network, including without limitation through a hard-wired connection, for example employing wires, cables, or a docking station or docking connector, for employing a connection including without limitation USB, IEEE 1394, serial, parallel, or SCSI, or a wireless connection, for example employing infrared, RF, IEEE 802.11, Bluetooth, IEEE 802.15, or Wi-Fi.

In an embodiment of the invention, a cover encloses the fingerprint acquisition pad. The cover may be secured using various mechanisms, for example, without limitation, a tab-and-slot connector, latch, spring latch, adhesive tape, or security tape. The cover may be secured prior to fingerprint acquisition and/or after fingerprint acquisition.

Figure 2:
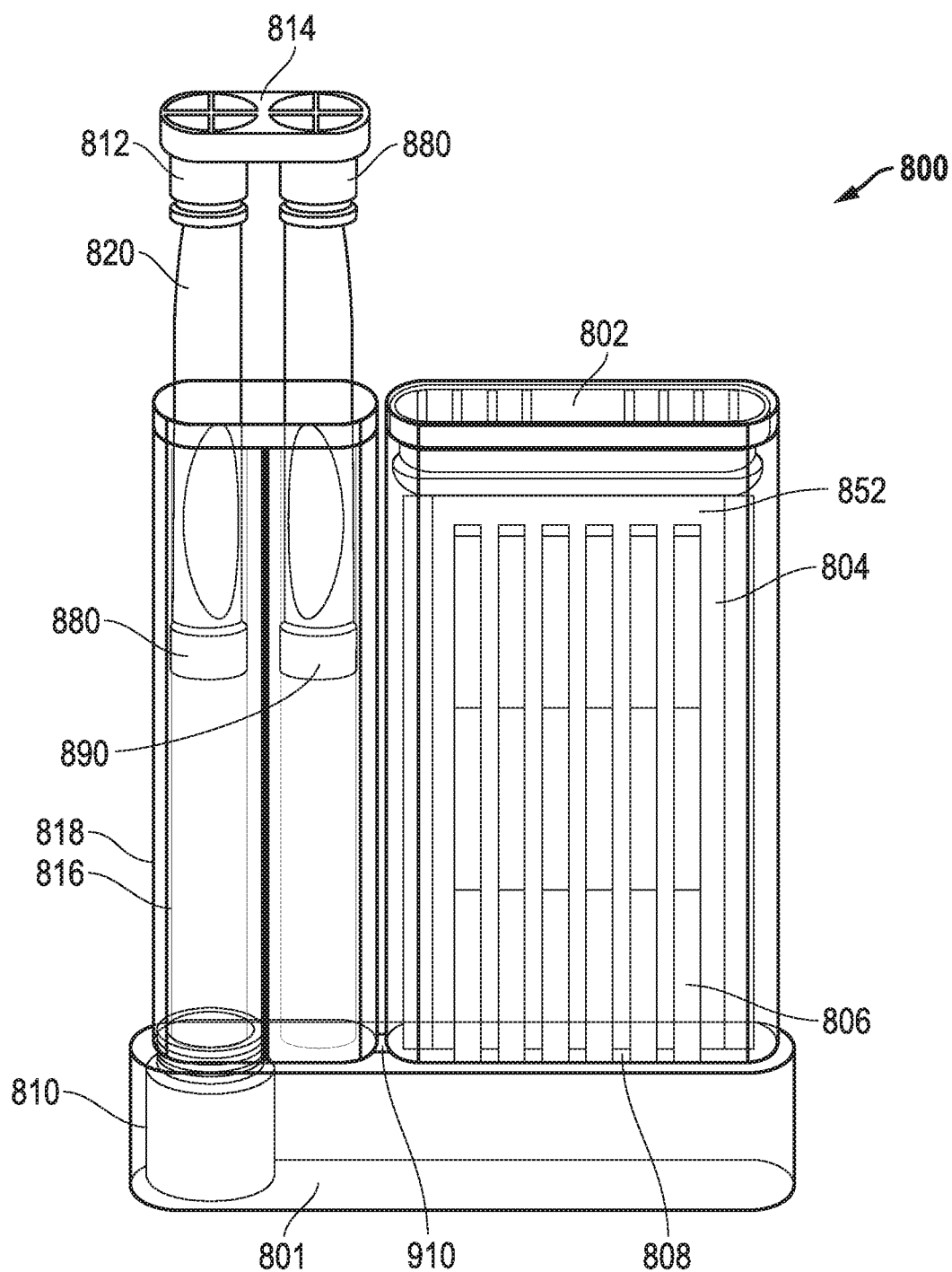
FIG. 2 depicts a perspective view of a fluid collection and analyte testing device in accordance with an embodiment of the present invention.
Figure 3:
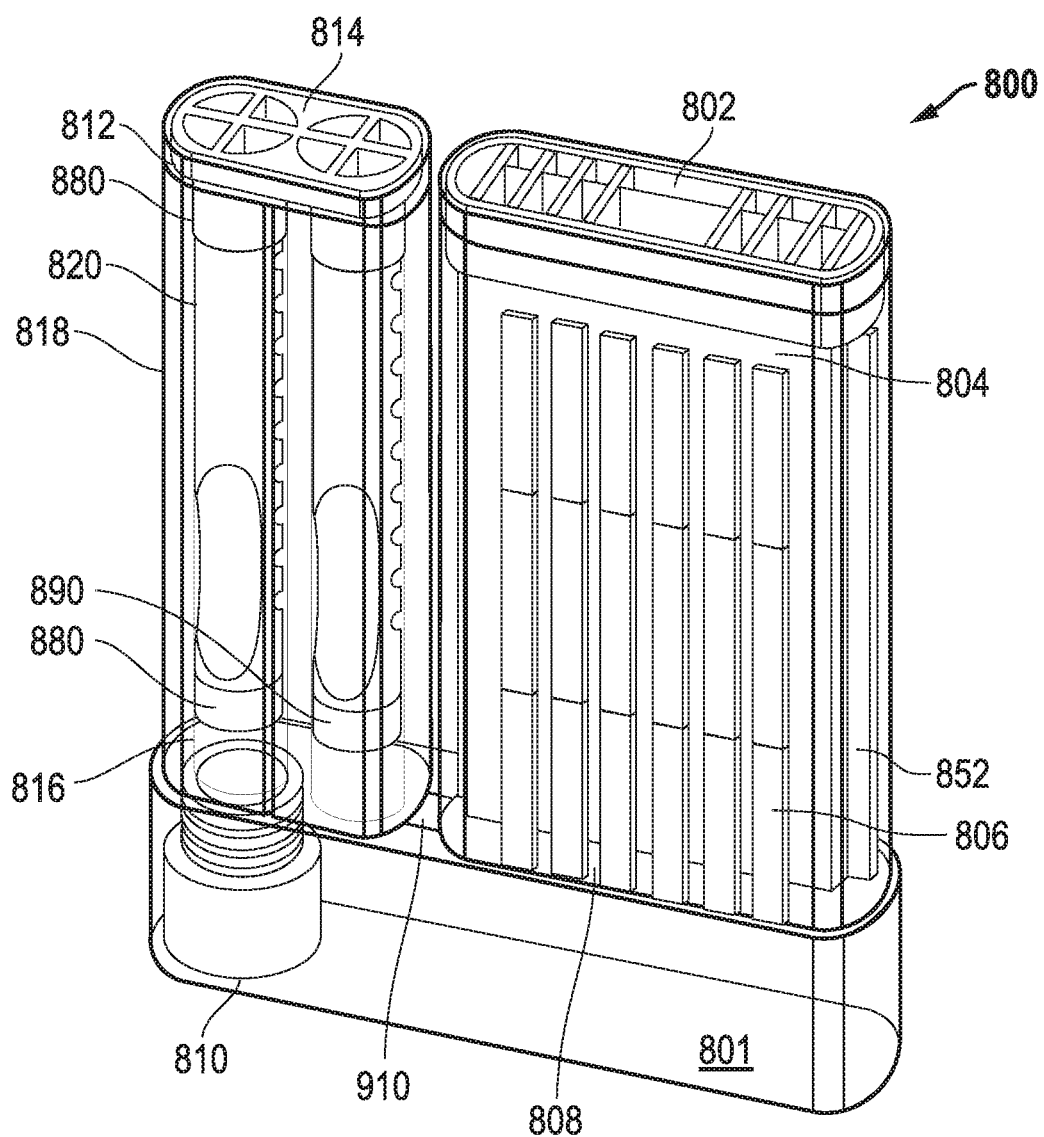
FIG. 3 depicts a perspective view of a fluid collection and analyte testing device in accordance with an embodiment of the present invention.
Figure 4:
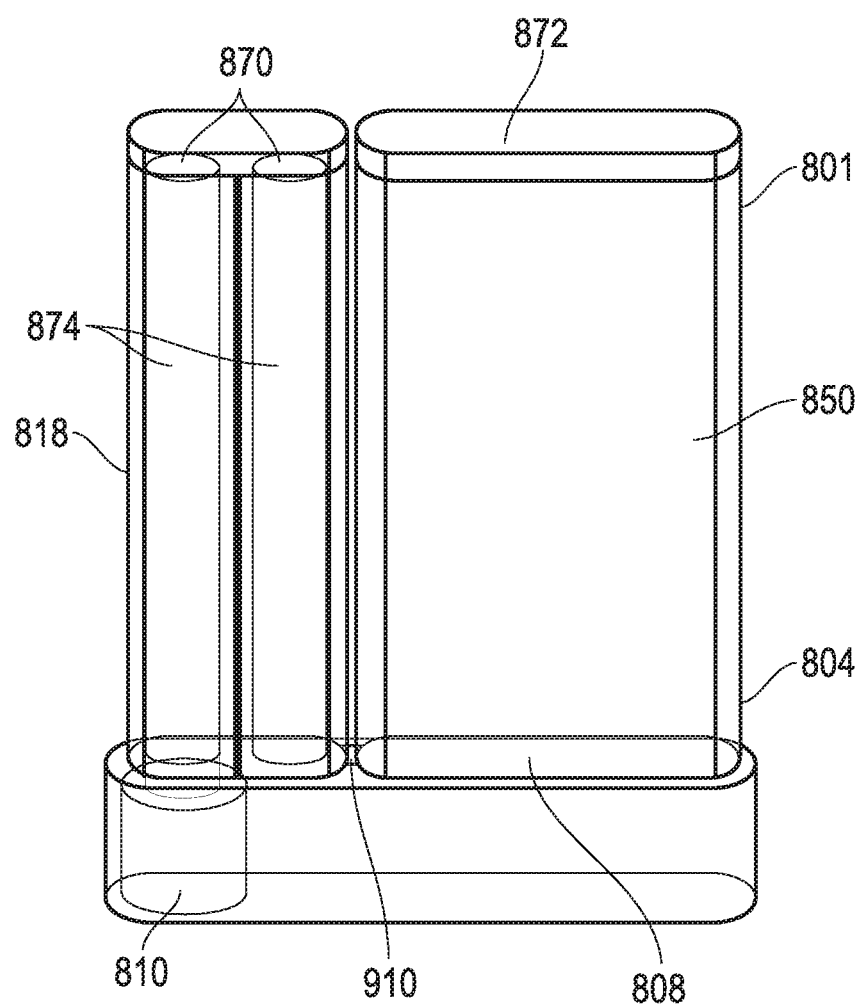
FIG. 4 depicts a perspective view of a housing of a fluid collection and analyte testing device in accordance with an embodiment of the present invention.
Figure 5:
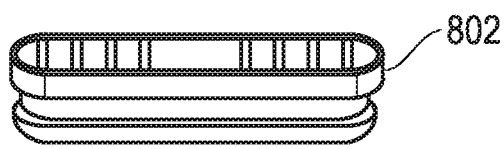
FIG. 5 depicts a perspective view of a test cartridge cap of a fluid collection and analyte testing device in accordance with an embodiment of the present invention.
Figure 6:
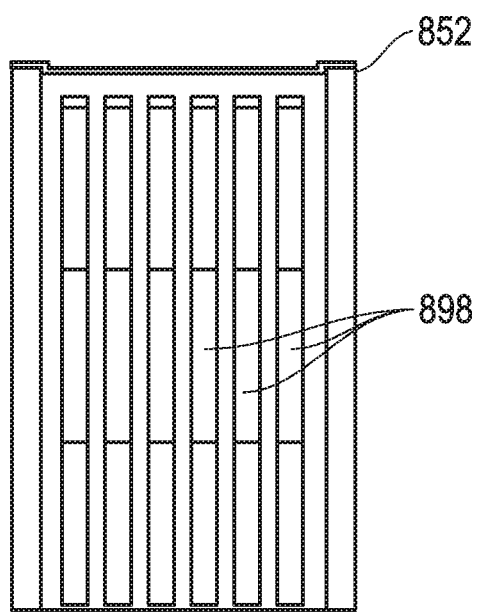
FIG. 6 depicts a front view of a dual surface test cartridge with test strip holders back-to-back of a fluid collection and analyte testing device in accordance with an embodiment of the present invention.
Figure 7:
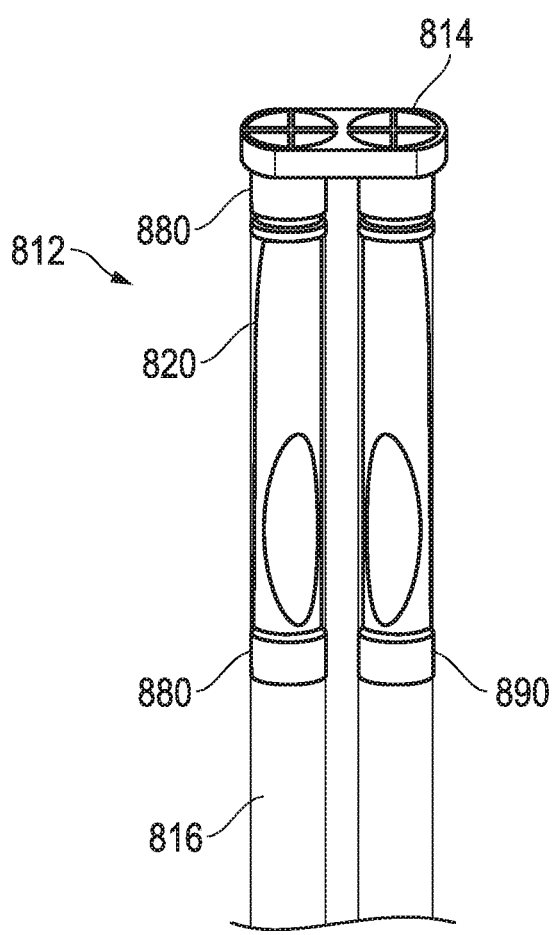
FIG. 7 depicts a perspective view of a split sample (dual sample) fluid collector of a fluid collection and analyte testing device in accordance with an embodiment of the present invention.
Figure 8:
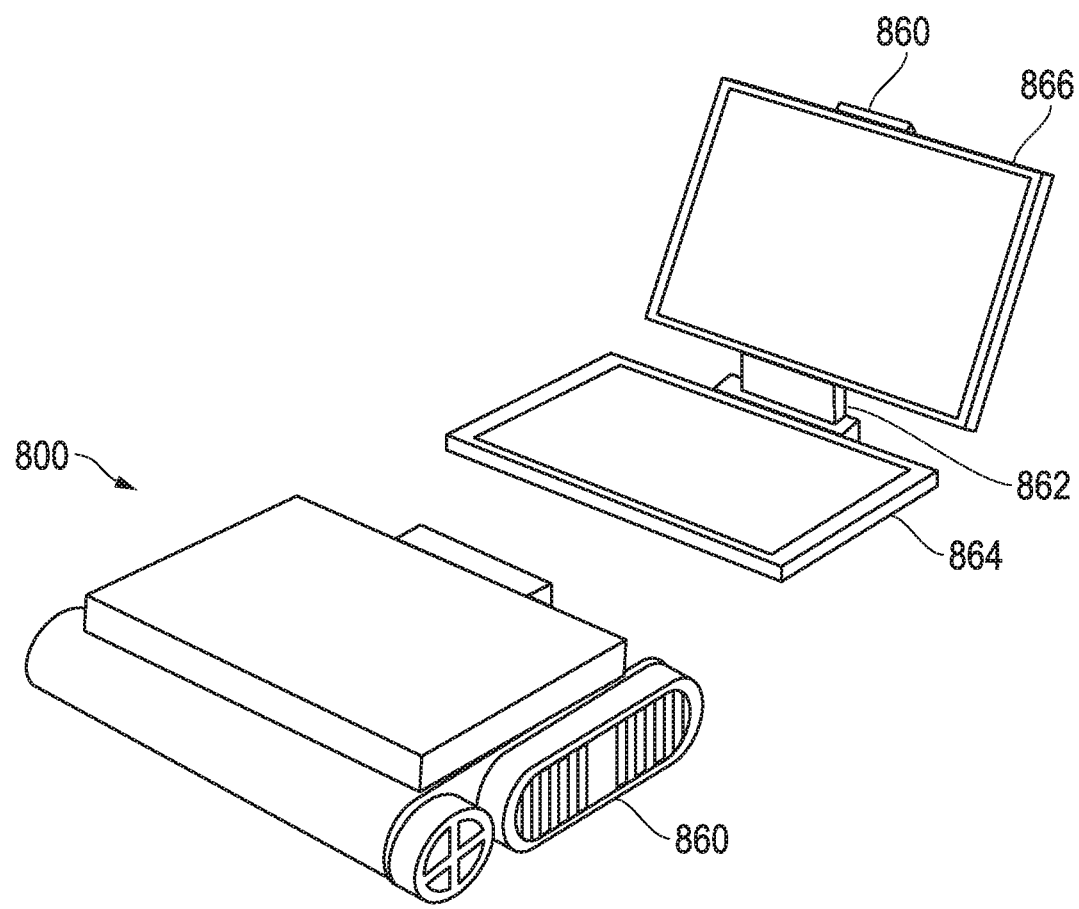
FIG. 8 depicts perspective view of a fingerprint assembly of a fluid collection and analyte testing device in accordance with an embodiment of the present invention.
Figure 9:
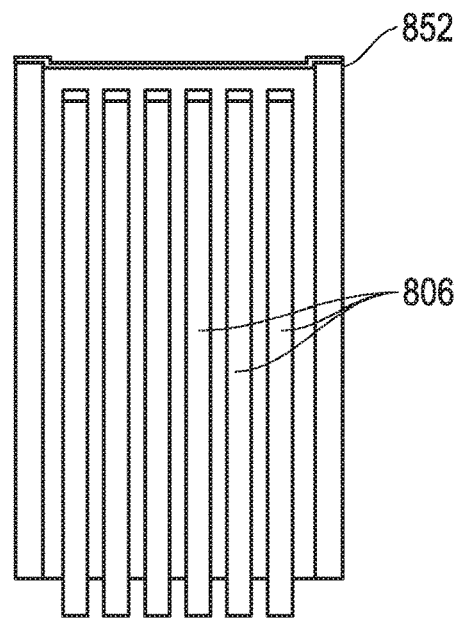
FIG. 9 depicts a front view of a dual surface test cartridge with test strips back-to-back of a fluid collection and analyte testing device in accordance with an embodiment of the present invention.
Figure 10:
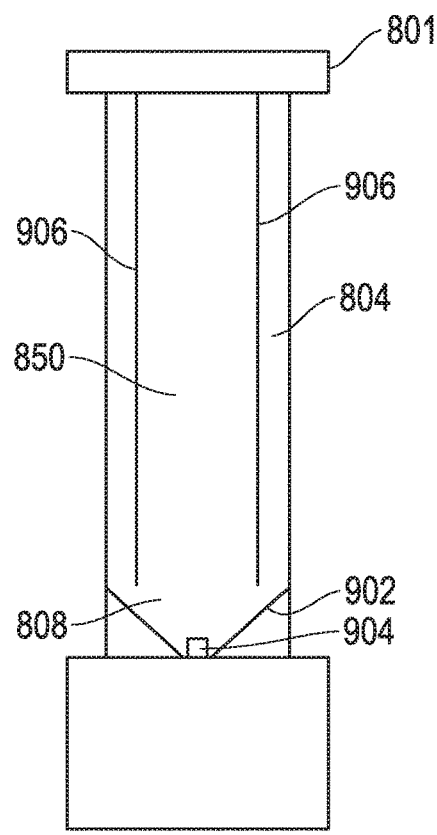
FIG. 10 depicts a cross-sectional end view of a housing of a fluid collection and analyte testing device in accordance with an embodiment of the present invention.

Referring to FIGS. 1-10, a fluid collection and analyte testing device according with embodiments of the invention are shown. In one embodiment, an analyte testing device 800 includes a fluid collector 812, to collect a fluid sample from a test subject, and a housing 801 to test and retain the fluid sample. The fluid collector 812 may include single or multiple collectors for the collection of the fluid sample. In one embodiment of the invention, a dual-swab split sample testing device, the fluid collector 812 includes a dual collector or a two-prong collector with prongs that are substantially identical, however, a wide variety of modifications to the prongs may be implemented without detracting from the spirit of the invention, including but not limited to, prongs of varying size, shape and materials. Each prong of the fluid collector 812 includes an upper segment 820 having an upper surface, a closure member 814, and sealing members 880; a compression member 890; and a collector 816 made from an absorbent material. A wide variety of absorbent materials capable of acquiring and storing a fluid sample may be used without detracting from the spirit of the invention, including but not limited to a swab, a sponge, and a material that dissolves subsequent to collection of the sample. In one embodiment of the invention, the absorbent material may be saturated with a saliva-producing substance to aid in the collection of the fluid sample. Additionally, the collector 816 may include a sufficiency or visual indicator to indicate when a sufficient amount of the fluid sample is present in the collector 816. U.S. Pat. No. 9,198,641 entitled "Specimen Sample Collection System" describes one prior art sufficiency or visual indicator system and is hereby incorporated by reference. The fluid collector 812 receives a fluid sample from a test subject and temporarily stores the fluid sample until it is transferred to the housing 801. In one embodiment of the invention, the fluid collector 812 receives a fluid sample from a test subject to be used in a split sample fluid testing device.

One advantage of the inventions disclosed herein is the limited amount of test material needed for testing and retention. According to one embodiment of the invention, only four hundred eighty (480) microliters are required for the successful analysis of twelve (12) test strips, forty (40) microliters for each test strip and only seven hundred (700) microliters are required from each prong. The minimum retention amount necessary is approximately the same volume as needed for the test strips. This quantity of a sample is obtainable through the fluid collector described herein. For example, forty (40) by ten (10) millimeter cylindrical collectors 816 collected a fluid, as the test sample, in amounts set forth in the tables below.

TABLE 1

Single-Prong Sample Collection Amount

| Sample | Total Fluid Amount Collected (ml) | Fluid in Chamber after Extraction (ml) | Fluid Loss (ml) | Collection Time (seconds) |
|---|---|---|---|---|
| 1 | 1.7 | 1.23 | 0.47 | 67 |
| 2 | 1.5 | 1.13 | 0.37 | 89 |
| 3 | 1.66 | 1.31 | 0.35 | 73 |
| 4 | 1.48 | 1.11 | 0.37 | 105 |
| 5 | 1.36 | 1.04 | 0.32 | 114 |
| 6 | 1.71 | 1.29 | 0.42 | 101 |
| 7 | 1.65 | 1.33 | 0.32 | 113 |
| 8 | 1.36 | 1.03 | 0.33 | 97 |
| Average | 1.55 | 1.18 | 0.37 | 95 |

TABLE 2

Dual-Prong Sample Collection Amount

| Sample | Total Fluid Amount Collected (ml) | Fluid in 1$^{st}$ Chamber after Extraction (ml) | Fluid in 2$^{nd}$ Chamber after Extraction (ml) | Fluid Loss (ml) | Collection Time (seconds) |
|---|---|---|---|---|---|
| 1 | 3.67 | 1.01 | 1.34 | 1.32 | 106 |
| 2 | 3.07 | 1.07 | 1.08 | 0.92 | 128 |
| 3 | 3.23 | 1.22 | 1.10 | 0.91 | 145 |
| 4 | 2.92 | 1.17 | 0.98 | 0.77 | 183 |
| 5 | 3.10 | 1.22 | 1.19 | 0.69 | 124 |
| 6 | 2.78 | 1.14 | 1.05 | 0.59 | 152 |
| 7 | 3.11 | 1.10 | 1.10 | 0.91 | 181 |
| 8 | 2.96 | 1.12 | 1.08 | 0.76 | 133 |
| Average | 3.11 | 1.13 | 1.12 | 0.86 | 144 |

As shown in Tables 1 and 2, the fluid collector 816, according to an embodiment of the invention, on average collects an amount of fluid samples in excess of the amounts required for testing and/or retention in approximately ninety (90)-one hundred fifty (150) seconds. A wide range of collection amounts are anticipated, depending upon the testing requirements, without detracting from the spirit of the invention.

The housing 801 includes a sample receiving member 818 to receive the fluid collector 812. In one embodiment of the invention, the sample receiving member 818 includes two collection chambers 874 to receive the two-pronged fluid collector 812 through two openings 870, thus forming a split sample. The sample receiving member 818 is in fluid communication with a fluid sample retention member, such as a confirmation collection chamber 810, and a test cartridge member 804. The test cartridge member 804 includes a test cartridge chamber 850; a test cartridge 852; at least one membrane test strip 806 located on the test cartridge 852 to indicate the presence or absence of at least one analyte; and a test cartridge fluid reservoir 808 in fluid communication with the test cartridge 852 and the sample receiving member 818. In one embodiment of the invention, the housing 801 includes windows on the front, back or both sides of the housing 801 for viewing of the membrane test strip 806. A wide variety of housings 801 may be implemented without detracting from the spirit of the invention, including but not limited to forming the housing 801 from a clear material allowing the membrane test strips 806 to be viewed without a window. The test cartridge fluid reservoir 808 may be formed in a variety of shapes without detracting from the spirit of the invention, including a v-shaped chamber with a flat bottom 902 as shown in FIG. 28. The test cartridge fluid reservoir 808 with a flat bottom v-shaped chamber 902 allows the test cartridge 852 and membrane test strips 806 to fully engage the fluid sample while maintaining a small volume of the fluid sample. In one embodiment of the invention, the v-shaped chamber with a flat bottom 902 forms a volume of less than seven hundred (700) microliters. An opening 904 at the bottom of the second collection chamber 874 is in fluid connection via a channel 910 with the test cartridge fluid reservoir 808. A wide variety of connection mechanisms may be implemented to connect the second collection chamber 874 and the test cartridge fluid reservoir 808 without detracting from the spirit of the invention, including but not limited to, tubes, piping, channels molded or carved into the housing 801, or any other suitable structure.

In one embodiment of the invention, the sample receiving member 818 includes a first collection chamber 874 in fluid communication with the confirmation collection chamber 810 and a second collection chamber 874 in fluid communication with the test cartridge member 804. The first collection chamber 874 and the confirmation collection chamber 810 are not in fluid communication with any other elements or components of the housing 801, including the second collection chamber 874 and the test cartridge member 804. The second collection chamber 874 is in fluid communication with the test cartridge fluid reservoir 808, which is in fluid communication with the test cartridge 852 and the membrane test strips 806.

Once the fluid collector 812 receives a fluid sample from a test subject, the fluid collector 812 is inserted into the two collection chambers 874 in the sample receiving member 818, through two openings 870. The fluid sample is expelled by compressing the collector 816 between the compression member 890 of both prongs against the bottom surface of the lower portion of the two collection chambers 874, thereby releasing the entrapped fluid into the housing 801. The fluid sample from the test subject is delivered from the first collection chamber 874 to the confirmation collection chamber 810 and from the second collection chamber 874 to the test cartridge fluid reservoir 808. The fluid sample is only obtained a single time with the multiple or two-prong fluid collector 812 while maintaining fluid sample integrity through the collection, storage and analysis of the fluid sample with two distinct storage areas: the confirmation collection chamber 810 and the test cartridge fluid reservoir 808. Once the fluid collector 812 is secured within the housing 801, the fluid sample from the confirmation collection chamber 810 is not in fluid communication with the fluid sample in the test cartridge fluid reservoir 808. The confirmation collection chamber 810 fluid sample may be accessed by a third party as previously disclosed, typically subsequent to the testing of the fluid sample in the test cartridge fluid reservoir 808. In one embodiment of the invention, the confirmation collection chamber 810 is located below the first collection chamber 874. In another embodiment of the invention, the confirmation collection chamber is removable from the housing 801 after the fluid sample is extracted from the collector 812. The fluid collector 812 secures the fluid sample within the sample receiving member 818 with the sealing members 880 to form a seal between the fluid collector and the fluid collection chambers 874. In one embodiment, each prong of the fluid collector 812 includes sealing members 880 located near the top and bottom of the upper segment 820 to seal both of the two collection chambers 874. The sealing members 880 include sealing rings. The sealing rings may be attached at locations close to the top and bottom of the upper segment 820. Generally, the dimensions of sealing members 880, and the sealing rings 28, comport with the interior dimension of the two collection chambers 874 in order to prevent the sample from escaping through the openings 870. Additionally, the fluid collector 812 is secured by the locking closure member 814. In one embodiment of the invention, the locking closure member 814 includes at least one projection extending from the fluid collector 812 that cooperates with the at least one projection located on the inner surface of the sample receiving member 818, where such projections may include for example at least one locking tab and/or at least one annular ring. According to one embodiment of the invention, a closure member on the fluid collector 812 may form a sufficiently secure closure as to constitute means for securing the fluid collector 812 within the sample receiving member 818.

The test cartridge 852 includes slots for one or more membrane test strips 806. In one embodiment of the invention, the test cartridge 852 includes locations or slots for membrane test strips 806 on both the front and back of the test cartridge 852 in a back-to-back formation. The test cartridge 852 may include multiple locations for the membrane test strips 806 on either the front, back or both sides of the test cartridge 852. The test cartridge 852 may allow for a wide number of membrane test strips 806 to be attached to the test cartridge without detracting from the spirit of the invention, including but not limited to, six (6), twelve (12), or twenty-four (24) membrane test strips 806. A wide variety of attachment mechanism may be used to attach the membrane test strips 806 to the test cartridge 852 without detracting to the spirit of the invention, including but not limited to, slotted membrane test strip holders 898 on the test cartridge 852 and a protective sheet attached to the test cartridge 852 that covers and impedes movement of the test strip 806 from the test strip holders 898. After the membrane test strips 806 are attached to the test cartridge 852, the test cartridge 852 is inserted into the test cartridge chamber 850 through a test cartridge chamber opening 872 and is placed between test cartridge guides 906 on both ends of the test cartridge chamber 850. In one embodiment of the invention, the membrane test strips 806 extend beyond the test cartridge 852 into the test cartridge fluid reservoir 808. A test cartridge cap 802 is then inserted into the test cartridge chamber 850 to secure the test cartridge 852 within the housing 801. In one embodiment of the invention, the test cartridge cap 802 is fixedly attached to the test cartridge 852 prior to insertion into the test cartridge chamber 850 or the test cartridge cap 802 and the test cartridge 852 are formed from a continuous material. In another embodiment of the invention, the test cartridge cap 802 attaches to a top edge of the test cartridge chamber opening 872. Advantageously, different versions of the test cartridge 852 may be developed to test different combinations of analytes, thereby allowing the test administrator to select the appropriate analyte test suite at the test site. The test cartridge chamber 850, the test cartridge cap 802, or a combination of both may include a locking mechanism known to those skilled in the art to secure the test cartridge 852 within the test cartridge chamber 850, thereby preventing the removal of the test cartridge 852 from housing 801.

In one embodiment of the invention, the test strips 806 may indicate genomic or proteomic information such that certain DNA sequences or proteins may be detected that are genetic predispositions for certain diseases such as various forms of cancer, diabetes, etc.

The test cartridge 852 and test cartridge cap 802 may be made from a variety of materials without detracting from the spirit of the invention, including but not limited to, plastic, ceramic, metal, glass, wood, rubber, polymer, fiber-reinforced polymer, or any combination thereof. In one embodiment, the test cartridge 852 is formed from plastic and is approximately 70 millimeters in height, 40 millimeters in width, and 5 millimeters in thickness.

After the fluid sample has been expelled from the fluid collector 812 into the test cartridge fluid reservoir 808, the fluid sample encounters the proximal end of the membrane test strip 806 and begins to move upward towards the upper end of the membrane test strip 806 by capillary action. Each membrane test strip 806 generally indicates the presence or absence of at least one analyte. A single drug, or class of drugs, is indicated by each membrane test strip 806, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol. In one embodiment, the test strips 806 may be lateral flow test strips.

In one embodiment, the test cartridge chamber 850 and/or the test cartridge fluid reservoir 808 may be attached to an electrical device that supplies an electric current to the fluid sample. The electrical current may be used to separate elements within the fluid sample prior to testing of the fluid sample.

The housing may include an immunoassay-based fingerprint acquisition pad 860 to positively identify an individual associated with the fluid collection and analyte test. In one embodiment of the invention, the second collection chamber and/or the test cartridge fluid reservoir 808 may be in fluid communication with the immunoassay-based fingerprint acquisition pad 860. The immunoassay-based fingerprint acquisition pad 860 may be removably connected to the housing 801 or fixedly attached to the housing 801. The immunoassay-based fingerprint acquisition pad 860 is enclosed by a cover 866 that is held closed by closure member 864 and pivots into the opened position on the axis defined by the hinges 862. The door 866 may be secured after the fingerprint of the test subject has been acquired, using various locking mechanisms, including without limitation a tab-and-slot arrangement, or security tape.

The immunoassay-based fingerprint acquisition pad 860 may be a stand-alone apparatus connected to the housing 801 or the immunoassay-based fingerprint acquisition pad 860 may be in fluid communication with the test cartridge fluid reservoir 808. The immunoassay-based fingerprint acquisition pad 860 in fluid communication with the test cartridge fluid reservoir 808 functions as previously disclosed.

In an embodiment of the invention, the immunoassay-based fingerprint acquisition pad 860 includes a compressible, porous reaction medium, having a control zone and a plurality of reaction zones, arranged on a porous support. The control zone includes a control reagent to identify the fluid sample donor, and each reaction zone includes a reaction reagent to determine the presence of a specific analyte in the fluid sample. The control reagent includes a member of a predetermined ligand/receptor binding pair. Similarly, each reaction reagent includes a member of a predetermined ligand/receptor binding pair. Various ligand/receptor binding pairs for use within the control and reaction zones are discussed within the '863 and '815 patents.

In an embodiment of the invention, the immunoassay-based fingerprint acquisition pad 860 is fluidically coupled to the collection chamber 874. A signal-producing agent, located on upper surface of the porous support or the lower surface of the reaction medium, mixes with the fluid sample provided to the immunoassay-based fingerprint acquisition pad 860. The production of an image or pattern which identifies the person providing the sample is accomplished by applying a fingertip to the upper surface of the reaction medium and compressing the reaction medium so that the fluid sample/signal-producing agent mixture permeates the reaction medium, and allowing the control zone ligand/receptor reaction to take place so that the members of this immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Although the invention is described herein with reference to specific embodiments, various modifications and changes can be made without departing from the scope of the invention as set forth in the claims below. The combination of embodiments is expressly anticipated, unless the embodiments and specifically mutually exclusive. A claimed invention may include multiple embodiments as disclosed herein. Accordingly, the specification and figures are to be regarded in an illustrative rather than a restrictive sense, and all such modifications are intended to be included within the scope of the invention. Any benefits, advantages, or solutions to problems that are described herein with regard to specific embodiments are not intended to be construed as a critical, required, or essential feature or element of any or all the claims.

From time-to-time, the invention is described herein in terms of these example embodiments. Description in terms of these embodiments is provided to allow the various features and embodiments of the invention to be portrayed in the context of an exemplary application. After reading this description, it will become apparent to one of ordinary skill in the art how the invention can be implemented in different and alternative environments. Unless defined otherwise, all technical and scientific terms used herein have the same meaning as is commonly understood by one of ordinary skill in the art to which this invention belongs.

The preceding discussion is presented to enable a person skilled in the art to make and use the invention. The general principles described herein may be applied to embodiments and applications other than those detailed below without departing from the spirit and scope of the invention as defined by the appended claims. The invention is not intended to be limited to the embodiments shown, but is to be accorded the widest scope consistent with the principles and features disclosed herein.

In addition, while a particular feature of the invention may have been disclosed with respect to only one of several embodiments, such feature may be combined with one or more other features of the other embodiments as may be desired. It is therefore, contemplated that the claims will cover any such modifications or embodiments that fall within the true scope of the invention.

The various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the invention. In addition, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more", "at least", "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Unless stated otherwise, terms such as "first" and "second" are used to arbitrarily distinguish between the elements such terms describe. Thus, these terms are not necessarily intended to indicate temporal or other prioritization of such elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the field or any related fields are intended to be within the scope of the following claims.

One skilled in the art will recognize that different embodiments may be formed in a similar manner having different characteristics depending upon need, performance, or some other criteria. It will thus be appreciated by those skilled in the art that changes could be made to the embodiments described above without departing from the broad inventive concept thereof. It is understood, therefore, that the invention disclosed herein is not limited to the particular embodiments disclosed, but it is intended to cover modifications within the spirit and scope of the present invention as defined by the appended claims.

Although this invention has been described in conjunction with specific embodiments thereof, many alternatives, modifications and variations will be apparent to those skilled in the art. Accordingly, the embodiments of the invention as set forth herein are intended to be illustrative, not limiting. Various changes may be made without departing from the true spirit and full scope of the invention as set forth herein.

What is claimed is:

1. An apparatus for testing a fluid sample comprising:
    a sample receiving member having an opening for receiving a fluid sample, wherein the sample receiving member includes at least first and second sample collection chambers, and a sample retention member in fluid communication with the first sample collection chamber to retain a portion of the fluid sample; and
    a test cartridge member in fluid communication with only the second sample collection chamber to indicate the presence or absence of at least one analyte in the fluid sample;
    wherein the test cartridge member comprising a test cartridge further comprises a front set of test strip slots and a back set of test strip slots.

2. The apparatus of claim 1, wherein the test cartridge comprises at least one test strip located in at least one of the front and back sets of test strip slots.

3. The apparatus of claim 2, wherein the test cartridge member comprises test cartridge chamber and a test cartridge fluid reservoir in fluid communication with the sample receiving member, wherein the test cartridge is inserted into the test cartridge chamber and wherein the at least one test strip is in fluid communication with the test cartridge fluid reservoir.

4. The apparatus of claim 3, wherein the test cartridge fluid reservoir is a v-shaped chamber with a flat bottom.

5. The apparatus of claim 4, wherein the v-shaped chamber with a flat bottom forms a volume of less than or equal to four hundred eighty (480) microliters.

6. The apparatus of claim 3, wherein the test cartridge is inserted into the test cartridge member.

7. The apparatus of claim 3, wherein a plurality of test strips are inserted into the front and back sets of test strip slots and wherein the plurality of test strips are in fluid communication with the test cartridge fluid reservoir.

8. The apparatus of claim 7, wherein the front set of test strip slots comprise at least six test strip slots and wherein the back set of test strip slots comprise at least six test strip slots.

9. The apparatus of claim 1, wherein the test cartridge member comprises a cap to secure the test cartridge.

10. An apparatus for testing a fluid sample comprising:
    a sample receiving member having an opening for receiving a fluid sample, wherein the sample receiving member includes at least first and second sample collection chambers, and a sample retention member in fluid communication with the first sample collection chamber to retain a portion of the fluid sample and a test cartridge member in fluid communication with only the second sample collection chamber to indicate the presence or absence of at least one analyte in the fluid sample.

11. An apparatus for testing a fluid sample comprising:
a sample receiving member having an opening for receiving a fluid sample, wherein the sample receiving member includes at least first and second sample collection chambers, and a sample retention member in fluid communication with the first sample collection chamber to retain a portion of the fluid sample; and
a test cartridge member in fluid communication with only the second sample collection chamber to indicate the presence or absence of at least one analyte in the fluid sample.

12. The apparatus of claim 1, wherein said first and second sample collection chambers are configured to receive a pronged fluid collector.

* * * * *